US00PP09797P

United States Patent [19]

Kamemoto et al.

[11] Patent Number: Plant 9,797

[45] Date of Patent: Feb. 4, 1997

[54] ANTHURIUM CULTIVAR NAMED 'TROPIC FIRE'

[75] Inventors: Haruyuki Kamemoto; Adelheid R. Kuehnle, both of Honolulu, Hi.

[73] Assignee: University of Hawaii, Honolulu, Hi.

[21] Appl. No.: 484,793

[22] Filed: Jun. 7, 1995

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

P.P. 9,080 3/1995 Hope ..... Plt./88.1

*Primary Examiner*—James R. Feyrer

*Attorney, Agent, or Firm*—Flehr, Hohbach, Test, Albritton & Herbert; Richard F. Trecartin; Jan P. Brunelle

[57] ABSTRACT

Tropic Fire is primarily characerized by an attractive dark green foliage which highlights its vivacious, glossy, bright red spathe carried about 90° from the flower stem axis. The spathe has open lobes, which are flat or slightly recurved, and a contrasting yellow upright spadix. Tropic Fire is resistant to anthracnose (spadix rot) and is tolerant to the bacterial blight. It propagates easily and forms multiple high-yielding flowering shoots rapidly, making it potentially well-suited for cut flower and flowering potted plant production.

2 Drawing Sheets

SUMMARY OF THE INVENTION

The invention relates to a new and distinct cultivar of Anthurium, botanically known as *Anthurium andraeanum*, and hereinafter referred to by the cultivar name 'Tropic Fire'.

Tropic Fire is a product of the anthurium breeding program of the University of Hawaii, Honolulu, Hi. It was discovered and selected in June 1989 from a cross made on Jan. 27, 1987 between a species hybrid and a cultivated variety developed and patented by the University of Hawaii. The female parent, designated A494, is a cross between *A. andraeanum* and *A. antioquiense*. The pollen parent is known as 'Kalapana' (described in U.S. Plant Pat. No. P.P. 8,320). Plants were subsequently asexually reproduced on the facilities of the University of Hawaii by research technicians under our direct supervision The reproduction techniques used were separation of suckers, taking top cuttings, and meristem tissue culture. All propagations that flowered have been true to the original type in plant and flower characteristics, demonstrating that the combination of characteristics as herein disclosed are maintained through successive generations.

The asexually reproduced cultivars have several desirable horticultural characteristics, including fast growth, ease of micropropagation, bright red spathe, dark green foliage, high flower field, excellent vase life, resistance of the spadix to anthracnose (caused by *Colletotrichum gloesporioides*), and tolerance to the bacterial blight (caused by *Xanthomonas campestris* pv. *dieffenbachiae*).

The following combination of traits distinguishes Tropic Fire as a new cultivar distinct from other Anthurium varieties, including the parent plants from which it was derived:

1. The bright red spathe (approximately R.H.S. Colour Chart 47A on the upper surface, 46B-C on the lower surface) is about 13 cm long and about 9 cm wide. It has glossy, open lobes, with tapered and occasionally twisted margins towards the apex. The margins are essentially complete, with only an occasional spathe having an indentation in the margin. The spathe is bilaterally symmetrical. Old flowers remain red, glossy, and attractive on the plant.

2. The spadix is about 6.5 cm long and about 0.8 cm in diameter. It is upright, yellow (approximately R.H.S. Color Chart 11A) upon opening of the spathe, turning creamy white with maturity, and is resistant to anthracnose.

3. The peduncle ranges from about 48 to 61 cm in length, is erect, and carries the spathe above the foliage.

4. The leaf blade of a fully mature, 4-year-old plant is about 30.5 cm long and about 18 cm wide. It is heart-shaped, and glossy green (approximately R.H.S. Colour Chart 139A on the upper side, and 146A on the underside).

5. The plant is tolerant to bacterial blight.

6. Micropropagation using conventional methods is fast, with rapid off-shoot production and ease of establishment ex vitro.

BRIEF DESCRIPTION OF THE PHOTOGRAPHS

The new cultivar is illustrated by the accompanying color photographs in which:

FIG. 1 is a front view which shows a representative flower of the new cultivar; and FIG. 2 is a front view which shows representative plant growth habit and carriage of the flower.

The colors are as accurate as is reasonably possible with color illustrations of this type.

DETAILED DESCRIPTION OF THE NEW CULTIVAR

Figure 1:
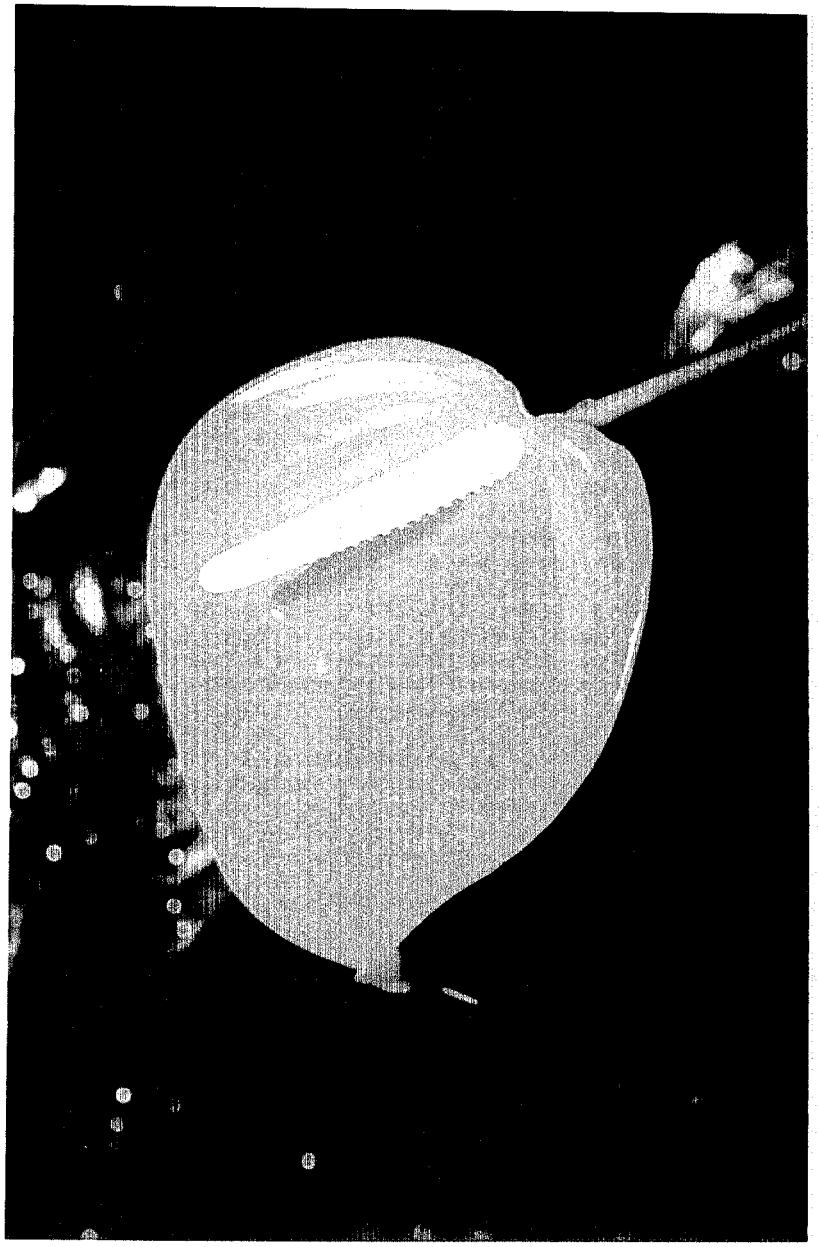
Figure 2:
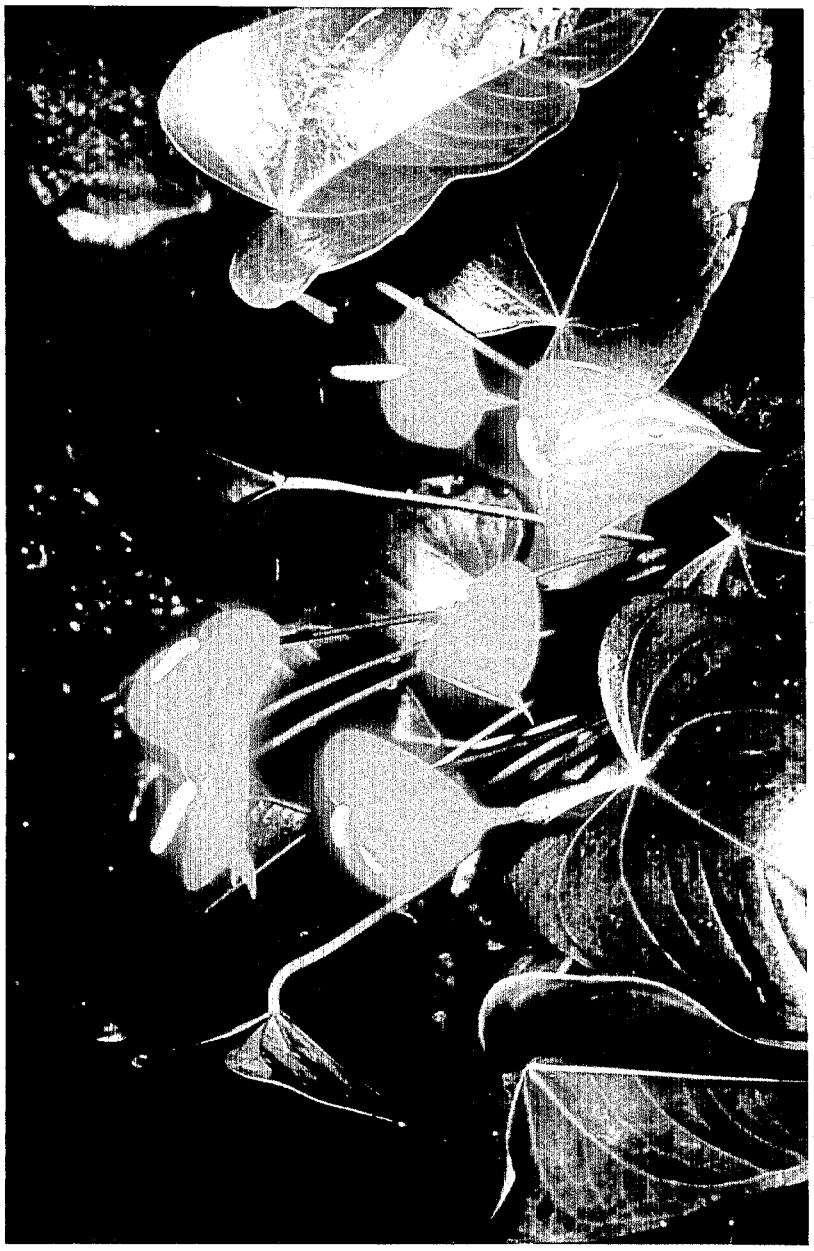

The following observations, measurements and values describe the new cultivar grown in Honolulu, Hi., under shadehouse conditions which closely approximate those generally in use in Anthurium horticultural practices:

Origin:

*Male parent.*—'Kalapana' (U.S. Plant Pat. No. P.P. 8,320), a red obake cultivar of *Anthurium andraeanum* patented in 1993 by the University of Hawaii.

*Female parent.*—A494 (*A. andraeanum*×*A. antioquiense*).

Classification: *Anthurium andraeanum*, cv. 'Tropic Fire'.

Plant: A three year old plant grown in a 20 cm pot has a height of about 61 cm and is about 46 cm wide.

Leaves:

*Form.*—The leaf blade is cordate with an acuminate tip (generally termed "heart-shaped"). The lobes are not touching.

*Size.*—The leaf blade of a mature sized plant is aout 30.5 cm long and about 18 cm wide.

*Petiole.*—The petiole is about 43 cm long and about 0.5 cm in diameter.

*Color.*—The upper surface of the leaf blade is glossy green (approximately R.H.S. Colour Chart 139A). The color of the lower surface of the leaf blade is approximately 146A on The R.H.S. Colour Chart.

Sucker production: Sucker production will vary with plants. Typically, 2–4 suckers are produced per year.

Inflorescence:

*Size.*—The mature flattened spathe is approximately 13 cm long and about 9 cm wide.

*Shape.*—The lobes are open and flat or slightly recurved. The margin is tapered occasionally twisted towards the apex. The margins are essentially complete, with only an occasional spathe having an indentation in the margin.

*Color.*—The spathe is a glossy, bright red (approximately R.H.S. Colour Chart 46A). Old flowers remain red, glossy, and attractive on the plant.

*Position.*—The spathe is carried at 90 degrees from the peduncle.

Spadix (reproductive organs):

*Size and shape.*—The spadix is about 6.5 cm long, about 0.8 cm wide, and is upright.

*Color.*—When the spathe unrolls, the spadix is yellow (approximately R.H.S. Color Chart 11A), turning creamy white with maturity.

*Reproductive organs.*—Not systematically observed but not believed to differ from those of other plants within the species.

*Fecundity.*—Not systematically determined at this time.

Peduncle (flower stem): The peduncle ranges in length from about 48 to 61 cm, is about 0.5 cm wide, and is erect.

Disease resistance: Tropic Fire is resistant to anthracnose (spadix rot); tolerant to the systemic phase of the bacterial blight in that the cultivar can become infected with *Xanthomonas campestris* pv. *dieffenbachiae* but the infection is usually localized and non-systemic.

Tolerance to full sun: Tropic Fire is typical of other Anthurium cultivars in that it is "shade-loving" and cannot tolerate full sun. In Hawaii, 80% shade is recommended.

Blooming habit: As with other Anthurium cultivars, Tropic Fire blooms year round provided proper light an temperature regimes are utilized.

General Observations

Tropic Fire has a glossy, bright red flower with contrasting yellow spadix highlighted by glossy green, medium-size leaves. The flowers have excellent longevity on the plant and as cut flowers (33 +/–6 days vase life). The plant has an upright growth habit and produces, on the average 7.2 flowers per growing point per year. The spathe is carried on a straight peduncle above the foliage. Tropic Fire is especially desirable because of its fast growth, high yield, flower color and gloss, attractive foliage, excellent flower life on the plant and in the vase, resistance to anthracnose (spadix rot) and tolerance to the systemic bacterial blight. Due to its unique combination of characteristics, Tropic Fire provides an excellent new anthurium cultivar for commercial cropping.

We claim:

1. A new and distinct cultivar of *Anthurium andraeanum* plant substantially as described and illustrated, by the cultivar name 'Tropic Fire' and characterized by the combined features of glossy, bright red spathe with tapered and occasionally twisted margins towards the apex, yellow spadix, straight peduncle carrying the spathe at 90 degrees from the peduncle and above the foliage, glossy green leaf blade with upright stature, high flower yield, excellent flower longevity, resistance to anthracnose (spadix rot), and tolerance to the systemic bacterial blight.

* * * * *